(12) United States Patent
McGann et al.

(10) Patent No.: US 11,478,596 B2
(45) Date of Patent: Oct. 25, 2022

(54) SYSTEM AND METHOD FOR HIGH FLOW OXYGEN THERAPY

(71) Applicant: COVIDIEN LP, Mansfield, MA (US)

(72) Inventors: Mark A. McGann, Ballybrittas (IE);
James P. Curley, Via Athlone (IE);
Paul J. Gallogly, Roscommon (IE);
Kieran M. Donlon, Athlone (IE);
Seamus P. Maguire, Athlone (IE);
Ronald Thiessen, Mission (CA); Erin F. McLaughlin, Langley (CA);
Richard Kauc, Milton (CA); Graham B. Fleming, Athlone (IE)

(73) Assignee: COVIDIEN LP, Mansfield, MA (US)

( * ) Notice: Subject to any disclaimer, the term of this patent is extended or adjusted under 35 U.S.C. 154(b) by 287 days.

(21) Appl. No.: 16/925,080

(22) Filed: Jul. 9, 2020

(65) Prior Publication Data

US 2021/0016040 A1 Jan. 21, 2021

Related U.S. Application Data

(60) Provisional application No. 62/875,827, filed on Jul. 18, 2019.

(51) Int. Cl.
*A61M 16/06* (2006.01)
*A61M 16/08* (2006.01)
(Continued)

(52) U.S. Cl.
CPC .... *A61M 16/0672* (2014.02); *A61M 16/0096* (2013.01); *A61M 16/0434* (2013.01);
(Continued)

(58) Field of Classification Search
CPC .......... A61M 16/0672; A61M 16/0666; A61M 16/0096; A61M 16/0434; A61M 16/0461;
(Continued)

(56) References Cited

U.S. PATENT DOCUMENTS 3,915,173 A * 10/1975 Brekke ............ A61B 17/12181
128/207.18
4,274,417 A 6/1981 Delpy
(Continued)

FOREIGN PATENT DOCUMENTS

WO 1994021163 A1 9/1994

OTHER PUBLICATIONS

"High flow oxygen therapy," Hamilton Medical AG, 2018, 4 pgs.
(Continued)

*Primary Examiner* — Colin W Stuart
*Assistant Examiner* — Douglas Y Sul (57) ABSTRACT

A method of method of high flow oxygen therapy (HFOT) and carbon dioxide ($CO_2$) monitoring includes delivering high flow oxygen therapy (HFOT) via a central lumen of a nasal cannula, the nasal cannula comprising a proximal end, a distal end positioned within a pharynx region of a patient's airway, and the central lumen and a sampling lumen formed within a wall of the nasal cannula. The method also includes receiving sampled exhaled breath of the patient via the sampling lumen at a $CO_2$ monitor, wherein the sampling lumen is configured to sample the exhaled breath at the pharynx region through the CO2-permeable membrane and direct the sampled exhaled breath to a $CO_2$ monitor fluidly coupled to the sampling lumen and determining a level of $CO_2$ in the exhaled breath using the $CO_2$ monitor.

19 Claims, 7 Drawing Sheets

(51) Int. Cl.
    *A61M 16/04*      (2006.01)
    *A61M 16/00*      (2006.01)
    *A61B 5/083*      (2006.01)

(52) U.S. Cl.
    CPC ...... *A61M 16/0461* (2013.01); *A61M 16/085* (2014.02); *A61B 5/0836* (2013.01); *A61M 2202/0208* (2013.01); *A61M 2210/065* (2013.01); *A61M 2230/432* (2013.01)

(58) Field of Classification Search
    CPC ...... A61M 2230/432; A61M 2210/065; A61B 5/082; A61B 5/0836; G01N 33/004; G01N 33/497
    See application file for complete search history.

(56) References Cited

U.S. PATENT DOCUMENTS

| | | | |
|---|---|---|---|
| 5,743,259 A | | 4/1998 | Kruse et al. |
| 5,937,858 A | * | 8/1999 | Connell ............... A61M 16/04 128/207.14 |
| 6,055,447 A | | 4/2000 | Weil et al. |
| 6,165,336 A | * | 12/2000 | Maki ................... G01N 33/497 427/244 |
| 6,394,093 B1 | * | 5/2002 | Lethi ................. A61M 16/0461 128/207.14 |
| 7,714,398 B2 | | 5/2010 | Ben-Barak et al. |
| 2005/0121038 A1 | * | 6/2005 | Christopher ...... A61M 16/0683 128/207.14 |
| 2005/0245836 A1 | * | 11/2005 | Star .................... G01N 27/4141 257/253 |
| 2007/0107728 A1 | * | 5/2007 | Ricciardelli ........... A61B 5/083 128/204.22 |
| 2008/0125635 A1 | | 5/2008 | Corl et al. |
| 2011/0230742 A1 | * | 9/2011 | Finneran ........... A61M 16/0484 128/207.14 |
| 2014/0150789 A1 | | 6/2014 | Flanagan et al. |
| 2015/0151094 A1 | * | 6/2015 | Lewer ............... A61M 16/0434 606/196 |
| 2016/0213281 A1 | | 7/2016 | Eckerbom et al. |

OTHER PUBLICATIONS

"Nomoline: Trouble-free sidestream gas analysis," Phasein AB, Sweden, 2009, 8 pgs.

Phillips, Justin S. et al.; "A Comparison of Different Techniques for Interfacing Capnography with Adults and Pediatric Supplemental Oxygen Masks," Respiratory Care, vol. 62, No. 1, Jan. 2017, pp. 78-85.

* cited by examiner

SYSTEM AND METHOD FOR HIGH FLOW OXYGEN THERAPY

CROSS-REFERENCE TO RELATED APPLICATIONS

The present application claims the priority to and the benefit of U.S. Provisional Application No. 62/875,827, entitled, "SYSTEM AND METHOD FOR HIGH FLOW OXYGEN THERAPY" and filed Jul. 18, 2019, the specification of which is hereby incorporated by reference for all purposes.

BACKGROUND

The present disclosure relates generally to systems and methods for high flow oxygen therapy (HFOT), and, in particular, devices for use in HFOT.

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the course of treating a patient, a tube or other medical device may be used to administer a fluid (e.g., air, oxygen, medication) into the patient's airway. For example, airway devices, such as oropharynx cannula (e.g., endotracheal tubes, tracheal tubes) and nasopharynx cannulas (e.g., tubes for nasal intubation), may be used to facilitate flow of one or more fluids into or out of the patient. Accordingly, such airway devices provide a flow passage between the patient's airway and the environment surrounding the patient (e.g., a gas source, a monitor). These airway devices may be part of a breathing circuit that allows a physician to facilitate breathing assistance or mechanical ventilation of the patient.

SUMMARY

In a first embodiment, a method of high flow oxygen therapy (HFOT) and carbon dioxide ($CO_2$) monitoring includes delivering high flow oxygen therapy (HFOT) via a central lumen of a nasal cannula, the nasal cannula comprising a proximal end, a distal end positioned within a pharynx region of a patient's airway, and the central lumen, and further comprising an inflatable cuff coupled to an exterior wall of the nasal cannula to anchor the distal end within the pharynx region and a sampling lumen formed within a wall of the nasal cannula, the sampling lumen terminating in a carbon dioxide ($CO_2$) permeable membrane positioned at or near the distal end of the nasal cannula, and wherein the $CO_2$-permeable membrane is selectively permeable to $CO_2$ relative to oxygen. The method also includes receiving sampled exhaled breath of the patient via the sampling lumen at a $CO_2$ monitor, wherein the sampling lumen is configured to sample the exhaled breath at the pharynx region through the $CO_2$-permeable membrane and direct the sampled exhaled breath to a $CO_2$ monitor fluidly coupled to the sampling lumen. The method also includes determining a level of $CO_2$ in the exhaled breath using the $CO_2$ monitor.

In a second embodiment, a high flow oxygen therapy (HFOT) airway device is provided, the HFOT airway device having a conduit including a proximal end and a distal end, wherein a length of the conduit extending between the proximal end and the distal end is between approximately 6.5 centimeters (cm) and approximately 23 cm. The HFOT airway device also includes an inflatable cuff coupled to an exterior wall of the conduit and positioned at or near the distal end; a sampling lumen disposed within a wall of the conduit and configured to be coupled to a carbon dioxide ($CO_2$) monitor; and a $CO_2$-permeable membrane disposed at the distal end of the conduit and covering a distal terminus of the sampling lumen.

In a third embodiment, a high flow oxygen therapy (HFOT) system is provided that includes a gas source providing a source of oxygen for delivery to a patient in high flow oxygen therapy (HFOT); a conduit coupled to the gas source that a first lumen extending between a proximal end and a distal end of the conduit, wherein the first lumen is configured to sample a patient's breath during exhalation The conduit also includes a second lumen adjacent to and fluidly coupled to the first lumen and configured to receive ambient air. The conduit further includes a carbon dioxide ($CO_2$) permeable membrane disposed on the distal end of the conduit. The $CO_2$ permeable membrane is configured to selectively allow passage of $CO_2$ gas from the patient's airway into the conduit during exhalation, wherein the $CO_2$-permeable membrane is selectively permeable to $CO_2$ relative to oxygen.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Breathing assistance systems may be used to deliver respiratory gases to patients and increase their blood oxygen levels. The type of airway device selected depends on the level of breathing assistance desired and/or the condition of the patient. During surgery, a patient may be fully sedated, and breathing assistance may be provided via mechanical ventilation. In some cases, the patient is intubated, and the patient's inspiration and exhalation are controlled by a mechanical ventilator that delivers respiratory gases via a tracheal tube. Tracheal tubes are typically inserted through a patient's mouth past the vocal cords. However, in some cases in which the surgeon desires unobstructed access to the patient's oral regions (e.g., orofacial surgery), nasotracheal intubation may be preferred. In some cases, breathing assistance systems may be used to assist patients who are not sedated, such as patients with asthmatic conditions, chronic obstructive lung disease, emphysema, or other medical conditions that affect a patient's ability to breathe normally.

For example, during mechanical ventilation, respiratory gases flow through the nasal or oral passageways during inhalation before entering the trachea and lungs, and flow out through the nasal and/or oral passageways during exhalation. This flow pattern may result in inefficiencies in gas circulation. The volume or space of the patient's respiratory system which contain inhaled air or respiratory gases that are not available for gas exchange is known as the dead space, and increases in dead space are associated with inefficiencies in respiratory gas delivery. Exhaled $CO_2$ from the patient's lungs may remain in the dead space of the patient's nasal cavity (rather than exiting through the mouth or nose), where it is available to flow back into the patient's lungs. Rebreathing of exhaled $CO_2$ remaining in the dead space of the airway may result in hypercapnia.

These inefficiencies can be exacerbated during high flow oxygen therapy (HFOT). The air flow patterns caused by the high flow rates associated with HFOT may encourage exhaled air to remain in the dead space rather than exiting the airway, by mixing $CO_2$ with incoming respiratory gases and causing re-breathing of $CO_2$. For example, during HFOT, humidified, heated respiratory gases are delivered to the patient's lungs at a flow rate of up to approximately 80 liters per minute (L/min). This high flow rate of the respiratory gases may create turbulent flow within the patient's airway, which mixes with $CO_2$ within the patient's airway and may result in re-circulation/re-breathing of the $CO_2$ into the patient's airway. As provided herein, HFOT provides oxygen flow of at least 10 L/min, at least 30 L/min, between 30-60 L/min, between 30-50 L/min, or between 40-80 L/min. Further, the flow rate may be a mean flow rate within a selected time window.

Provided herein are techniques for ventilation or oxygen therapy that reduce $CO_2$ rebreathing. The present techniques incorporate a nasal cannula configured such that, when inserted into the airway, a distal end of the cannula is positioned adjacent to the patient's soft palate (e.g., within a pharynx region) between the nasopharynx and the oropharynx. Sealing the airway between the nasopharynx and the oropharynx decreases a volume of dead space within the patient's airway and facilitates $CO_2$ washout via the patient's mouth. Further, delivering respiratory gases at a more distal location in or past the nasopharynx may bypass portions of the airway that are associated with dead space, and provide a more direct path for respiratory gases to reach the patient's lungs. In some instances, this positioning also causes a change in the flow characteristics of the respiratory gases into the airway to be more laminar, which may facilitate removal of exhaled $CO_2$ from the patient's airway. As provided herein, the nasal cannula may also include a distal inflatable cuff that is positioned to seal the nasal passageway above the delivery site of the respiratory gases, preventing exhaled $CO_2$ from entering the dead space of the nasal passageway while leaving the oral passageway open for exhalation. The cuff may be asymmetric and/or sized and shaped to fill the nasopharynx. In addition, the disclosed techniques may permit simultaneous HFOT therapy and sidestream $CO_2$ monitoring.

Figures 1, 2:
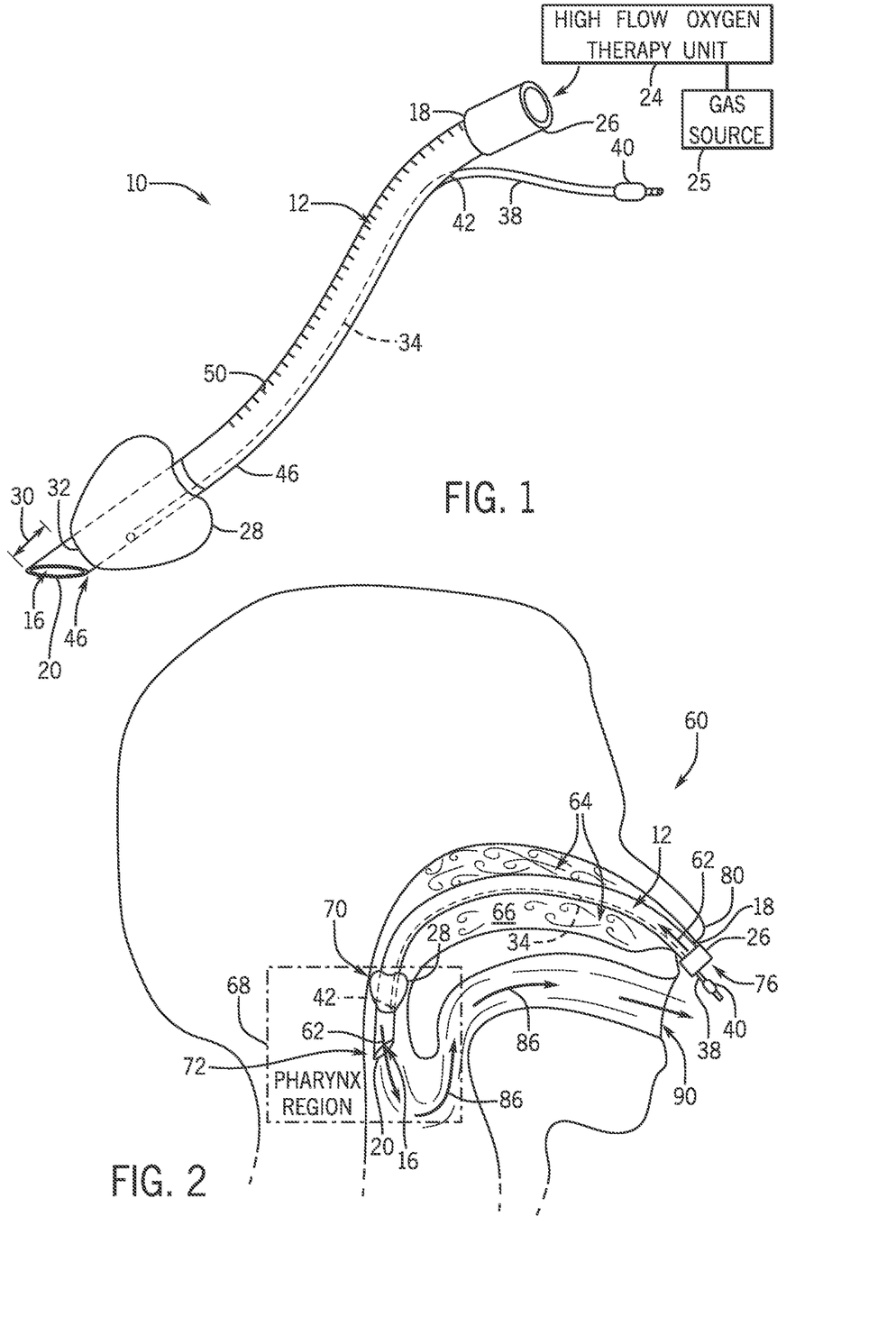
FIG. 1 is a perspective view of a cuffed nasal cannula, in accordance with an embodiment of the present disclosure.
FIG. 2 is a schematic of a patient intubated with the cuffed nasal cannula of FIG. 1, whereby the cuffed nasal cannula includes a connector adjacent to nares of the patient, in accordance with an embodiment of the present disclosure.

FIG. 1 illustrates an embodiment of a nasal cannula 10 that may be used for HFOT or various forms of mechanical ventilation in accordance with the present techniques. For example, the nasal cannula 10 may be inserted into a patient's nasal cavity to provide a pathway between the patient's nose (nasal opening) and lungs. The nasal cannula 10 includes a conduit 12 (e.g., a tubular body such as an extruded tube) having a lumen 16 extending between a proximal end 18 and a distal end 20 of the conduit 12. During HFOT, respiratory gases (e.g., a mixture of air and oxygen) flow through the lumen 16 and into the airway of the patient. That is, the lumen 16 forms a pathway between the patient's nose and lungs for delivery of the respiratory gases. The proximal end 18 of the conduit 12 includes a connector 26 (e.g., adapter) that removably couples the nasal cannula 10 to a respiratory/breathing apparatus (such as an HFOT unit 24) that is coupled to a gas source 25 and that supplies the respiratory gases. The HFOT unit 24 may be implemented as a standalone device or may be a ventilator that is capable of operating in a HFOT mode to deliver HFOT as well as in other modes to deliver other types of respiratory therapy. The HFOT unit may include integral control systems that control parameters, such as flow rate, related to HFOT. The connector 26 may include a standard 26 millimeter (mm) connector. However, any other suitably sized connectors may be used. As discussed in further detail below, in certain embodiments, the respiratory apparatus may include a monitoring system for monitoring one or more patient parameters. For example, the respiratory apparatus may include a carbon dioxide ($CO_2$) monitor (e.g., a capnograph) used to monitor end tidal $CO_2$ ($EtCO_2$) levels and/or tidal volume in exhaled breath of the patient.

In the illustrated embodiment, the nasal cannula 10 includes a cuff 28 positioned at the distal end 20 of the conduit 12. For example, the cuff 28 may be positioned adjacent to the distal end or a short distance 30 away from the distal end 20 (e.g., a terminus of the conduit 12). That is, a distal-most end 32 of the cuff 28 in its deflated state may be even with or separated from the distal end 20 by the distance 30. The distance 30 may be between approximately 1 centimeter (cm) and approximately 4 cm. The cuff 28 circumferentially surrounds the conduit 12 and may be inflated to an extent to seal against walls of a body cavity (e.g., against the soft palate and pharangeal wall between the nasopharynx and the oropharynx). Accordingly, when inflated, the cuff 28 anchors the nasal cannula 10 in position within the patient's airway. The cuff 28 may be inflated via an inflation lumen 34 coupled to an inflation tube 38, which in turn is connected to an inflation pilot balloon and valve assembly 40. The inflation lumen 34 terminates in an opening 42 (e.g., notch) on an outer wall 46 of the conduit 12 at the point of coupling the inflation lumen 34 to the inflation tube 38. The opening 42 allows fluid communication between the inflation pilot balloon and valve assembly 40 and an interior of the cuff 28 such that the cuff 28 may be inflated via the inflation lumen 34.

Additionally, it should be noted that the cuff 28 may be any suitable shape, such as a tapered shape, a barrel shape, conical or truncated conical, or combinations of these. The cuff 28 may be formed from materials having desirable mechanical properties (e.g., puncture resistance, pin hole resistance, tensile strength, and so forth) and desirable chemical properties (e.g., biocompatibility). For example, in one embodiment, the walls of the cuff 28 may be made of a polyurethane (e.g., Dow Pellethane® 2363-80A) having suitable mechanical and chemical properties. In other embodiments, the walls of the cuff 28 may be made of silicone or a suitable polyvinyl chloride (PVC). In certain embodiments, the cuff 28 may be generally sized and shaped as a high volume, low pressure (HVLP) cuff that may be designed to be inflated to pressures between about 15 centimeters (cm) $H_2O$ and 30 cm $H_2O$ to anchor the cuff 28 in position. In other embodiments, the cuff 28 may be generally sized and shaped as a low volume, high pressure (LVHP) cuff to anchor the cuff 28 in position. As further discussed herein, the cuff 28 may be asymmetric and/or sized and shaped to fit the nasopharynx. However, it should be understood that the disclosed conduit 12 may also be provided in an uncuffed (i.e., not including a cuff 28) configuration that may be desirable for patients with smaller airways.

In certain embodiments, the conduit 12 may include markings 50 along at least a portion of the outer wall 46. The markings 50 may provide a healthcare provider with an indication of how far into the nasal cavity and/or pharynx region of the patient's airway the conduit 12 is inserted. The markings 50 may include notches, numbers, hash marks, or any other suitable marking that provides a healthcare provider with an approximate position of the distal end 20 of the conduit 12 within the patient.

As discussed above, during HFOT, turbulent flow created by the high flow of oxygen into the patient's airway may increase buildup of $CO_2$. As such, an excess amount of $CO_2$ may remain in the dead space after exhalation. Therefore, rebreathing of the $CO_2$ during the next inhalation may increase, which may result in hypercapnia. However, as provided herein, by delivering respiratory gases via the nasal cannula 10 that extends into the pharynx region of the airway such that a terminus of the nasal cannula 10 is positioned between the nasopharynx and the oropharynx, the flow of oxygen may be laminar rather than turbulent. The laminar flow of the oxygen flowing into the patient's airway may improve $CO_2$ washout during HFOT by directing the $CO_2$ into and out of the patient's mouth, thereby decreasing buildup of $CO_2$ in dead spaces within the patient's airway.

For example, FIG. 2 is a side profile view of a patient 60 undergoing ventilation or oxygen therapy using the nasal cannula 10, in accordance with an embodiment of the present disclosure. As shown in the illustrated embodiment, the nasal cannula 10 provides a flow path for respiratory gases 62 (e.g., blend of air and oxygen) to enter into the patient's airway in a manner that bypasses the dead space in the breathing circuit. For example, during breathing, air 64 within a nasal cavity 66 of the patient 60 is not available for gas exchange. That is, the oxygen and the $CO_2$ in the air 64 within the nasal cavity 66 do not undergo gas exchange in a manner that would increase the patient's bloodstream oxygen levels. Accordingly, the nasal cavity 66 forms a dead space. By using the nasal cannula 10 to create a flow path for the respiratory gases 62, the dead space within the nasal cavity 66 may be bypassed, which improves the efficiency of the HFOT and mitigates rebreathing of $CO_2$.

While the embodiment illustrated FIG. 2 includes the cuff 28, the cuff 28 is optional. Accordingly, certain embodiment of the nasal cannula 10 are un-cuffed. It has be recognized that, by positioning the distal end 20 of the conduit 12 within a pharynx region 68, a flow of the respiratory gases 62 may be improved compared to shorter nasal cannulas that terminate at earlier points within the nasal cavity 66 (e.g., nasal prongs). For example, the flow of respiratory gases exiting from the shorter prong-type nasal cannulas may become turbulent and unstable. For example, when respiratory gases exit the prong-type nasal cannulas and enter into the interior volume formed by the nasal cavity, the respiratory gases expand to fill the relatively larger area within the nasal cavity. Therefore, efficient flow of the respiratory gases is disrupted, and the respiratory gas flows in a disordered manner (e.g., turbulent, in multiple directions) in the nasal cavity, which decreases the efficiency of the HFOT and delivery of respiratory gases to the lungs. However, as provided herein, providing an elongated HFOT nasal cannula that is sufficiently long such that a distal end (e.g., the distal end 20) is positioned between the nasopharynx 70 and the oropharynx 72 (i.e., in the pharynx region), the nasal cavity 66 may be bypassed and the flow of respiratory gases 62 exiting from the distal end 20 flows directly into the patient's throat. The patient's throat in this region has a similar configuration to the elongated HFOT nasal cannula in that it is tubular and maintains a more orderly (e.g., more laminar) flow of the respiratory gases 62. Therefore, by bypassing the nasal cavity 66, the flow of the respiratory gases 62 exiting the distal end 20 remains more smooth and laminar as compared to shorter devices (e.g., nasal prongs) that do not bypass the nasal cavity. The laminar flow into the patient's airway is more efficient in directing the respiratory gases 62 into the patient's lungs and maintaining the desired expiratory pressure within the lungs such that the efficiency of gas transfer into the patient's bloodstream is improved.

While such nasal cannulas 10 as provided are longer than prong-style cannulas, the nasal cannulas 10 as provided are also shorter than tracheal tubes (e.g., oral or nasal endotracheal tubes) used in mechanical ventilation. Further, the nasal cannulas 10 as provided do not seal the entire airway to provide a single entry/exit passage for respiratory gases in the manner of endotracheal tubes. In contrast, the nasal cannulas 10 as provided, when cuffed, seal the nasal cavity but leave the oral cavity unsealed to permit patient exhalation through the mouth to facilitate HFOT. When uncuffed, the nasal cannulas 10 provide direct flow from the distal end 20 and an exit path for exhaled gases through the oral cavity 90 that bypasses the nasal cavity 66, but permit some gas exfiltration through the nasal cavity 66.

Therefore, in accordance with an embodiment of the present disclosure, the nasal cannula 10 may have a length that is between approximately 20 percent and 60 percent shorter than existing right angle endotracheal tubes such that, when inserted, the distal end 20 is positioned at the desired location in the pharynx region 68. For example, a length of the nasal cannula 10, which extends between the distal end 20 and a proximal terminus 76, may be between approximately 11 centimeters (cm) and 23 cm for adult sizes and between approximately 6.5 cm and 20 cm for pediatric sizes. In one embodiment, the length of an adult nasal cannula 10 may be approximately 11 cm to approximately 13 cm with an inner diameter ranging from approximately 7.5 mm to approximately 9.5 mm. In one embodiment, the length of an adult nasal cannula 10 may be approximately 11 cm to approximately 20 cm with an inner diameter ranging from approximately 7.5 mm to approximately 9.5 mm.

Moreover, when the nasal cannula is cuffed, sealing the passage between the nasopharynx 70 and the oropharynx 72 may improve $CO_2$ washout and mitigate rebreathing of $CO_2$-rich exhaled air that remains within the dead space of the nasal cavity 66. This is based on improved $CO_2$ flushing in the presence of laminar flow versus decreased $CO_2$ flushing in the presence of turbulent flow. For example, the high flow rate (e.g., between approximately 30 L/min and 80 L/min) of the respiratory gases 62 entering the patient's airway through the nasal cannula 10 and that exhibit characteristic laminar flow tend to washout (e.g., flush) $CO_2$-rich exhaled gas 86 from the patient's airway via the patient's oral cavity 90. This is in contrast to more turbulent high flow respiratory gases delivered via a shorter prong-like nasal cannula, in which turbulent gases flowing into the nasal cavity mix with the $CO_2$-riched exhaled gas 86 in the nasal cavity. Turbulent mixing of exhaled gas 86 with newly delivered respiratory gases interferes with respiratory gas delivery as well as with efficient $CO_2$ washout, which may in turn lead to $CO_2$ rebreathing. For example, a portion of the incoming respiratory gases 62 may displace the $CO_2$-rich exhaled gas 86 such that the respiratory gases are pushed toward the patient's oral cavity 90 for release from the patient 60 rather than being delivered to the lungs. Accordingly, reducing the presence of turbulent gas flow, as in the disclosed techniques, leads to more efficient respiratory gas delivery, improved $CO_2$ washout, and decreased $CO_2$ rebreathing.

In certain embodiments, the nasal cannula 10 may include a second lumen that provides a passageway for the patient's exhaled breath to be released. That is, rather than exhaling through the oral cavity 90, the patient's exhaled breath may be exhaled through the second lumen. For example, the second lumen may be adjacent to the lumen 16 into which at least a portion of the $CO_2$-rich exhaled gas 86 may flow out of the patient's airway (e.g., the second lumen may have an opening at the proximal terminus 76 of the nasal cannula 10 that releases the $CO_2$-rich exhaled gas 86) during exhalation.

Figure 3:
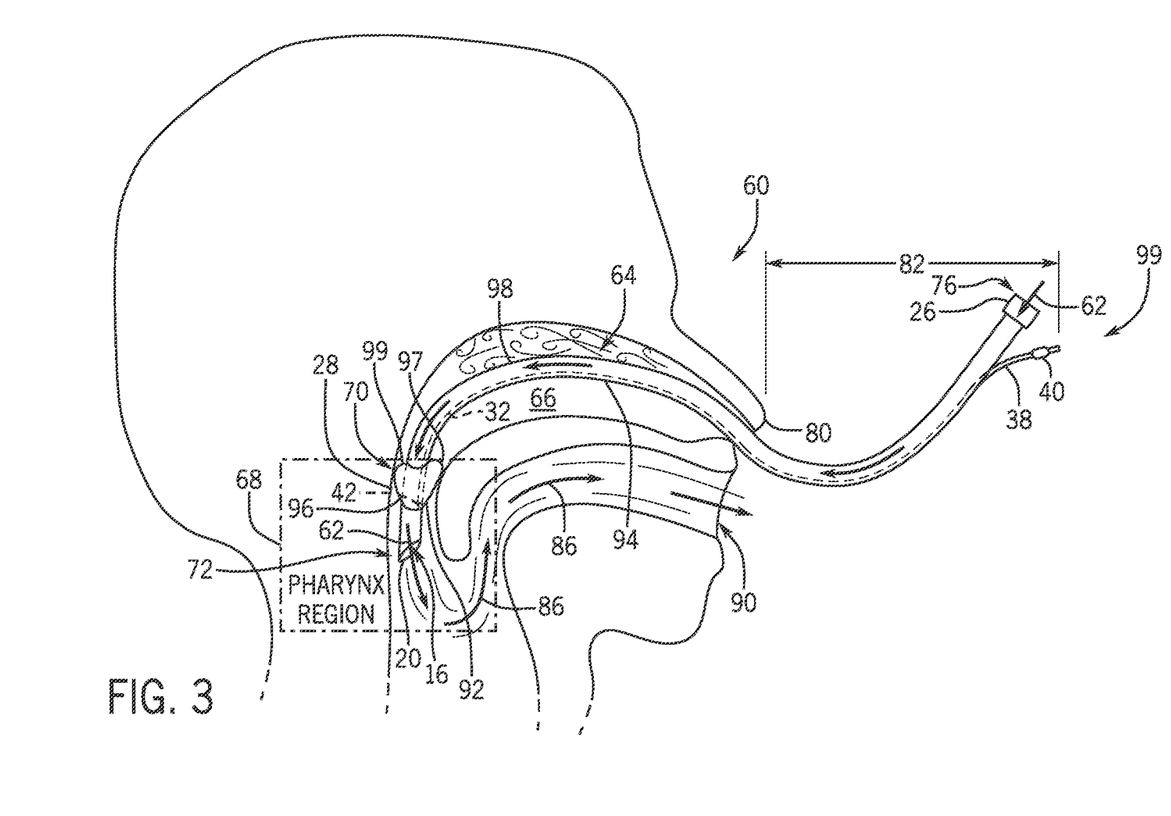
FIG. 3 is a schematic of a patient intubated with the cuffed nasal cannula of FIG. 1, whereby the cuffed nasal cannula includes a connector at a proximal end that is positioned away from nares of the patient, in accordance with an embodiment of the present disclosure.

In certain embodiments, a length of the nasal cannula 10 is such that, when the nasal cannula is properly positioned within the patient's airway (e.g., the distal end 20 is within the pharynx region 68), the proximal end 18 of the conduit 12 is adjacent to a nasal opening (e.g., nostril) of the nose 80 of the patient 60, as shown in FIG. 2. Positioning the proximal end 18 against or adjacent to the nose 80 of the patient 60 may provide a position that does not obstruct the patient's oral cavity 90 (e.g., mouth). Therefore, the oral cavity 90 of the patient may be accessible for administering oral medications, introducing a medical device (e.g., a visualization device, camera, or the like), and enable the patient 60 to speak. Additionally, placing the proximal end 18 of the conduit 12 adjacent to the nasal opening positions the connector 26 against the patient's skin, which may facilitate securing the nasal cannula 10 to the patient and mitigate movement, torqueing, and dislodging of the nasal cannula 10. However, in other embodiments, the proximal end 18 may be a distance 82 away from the nose 80 of the patient 60, as illustrated in FIG. 3. Having the proximal end 18 the 82 away from the nose 80 of the patient 60 may mitigate having the inserted device positioned to obstruct portions of the patient's face (e.g., the oral cavity 90 and/or nose 80). For example, the oral cavity 90 and the nares unoccupied by the nasal cannula 10 may be accessible to a caregiver for treatment of the patient 60 (e.g., administration of medications and/or imaging procedures).

In certain embodiments, the cuff 28 may be configured to fit within an irregularly-shaped nasopharynx 70. For example, the cuff 28 may be asymmetric about the axis of the lumen 16, such that a larger volume portion 92 of the cuff 28 is located adjacent to an interior curve 94 of the cannula 10 while a relatively smaller volume portion 96 is located adjacent an outside curve 98. This may be accomplished by providing a cuff 28 that has a single interior inflated region, but with an asymmetric cuff structure that permits asymmetric expansion. While lateral expansion within the trachea is bounded by contact with the tracheal walls, such asymmetric expansion may permit greater expansion distally and/or proximally in the larger volume portion 92 relative to the smaller volume portion 96. As result, a distance from a distal-most to a proximal-most point 97 of the larger volume portion 92 may be greater relative to that of the smaller volume portion 96. In the depicted embodiment, the proximal-most point 97 of the larger volume portion 92, when inflated, extends proximally past a proximal-most point 99 of the smaller volume portion 96 to provide the additional volume in the larger volume portion 92. However, other arrangements are contemplated. In an embodiment, the larger volume portion 92 includes a longer outer curve as compared to the smaller volume portion 96, which has a shorter curve. The larger volume portion 92 may expand more than the smaller volume portion 96 when the cuff 28 is inflated. In certain embodiments, the larger volume portion 92 may include a greater amount of cuff material compared to the smaller volume portion 96 to permit asymmetric expansion. By having a greater amount of cuff material, the larger volume portion 92 accommodates a larger volume of fluid, enabling the larger volume portion 92 to expand more than the smaller volume portion 96. In other embodiment, the larger volume portion 92 may be manufactured from a more flexible cuff material compared to the smaller volume portion 96. The differences in flexibility of the cuff material between the portions 92, 96 enable the larger volume portion 92 to expand more than the smaller volume portion 96. Such an arrangement may facilitate a funnel or tapering shape of the cuff 28. Further, the cuff 28 may also taper towards the distal end 20. For example, a size of the cuff 28 may decrease toward the distal end 20.

Figure 4:
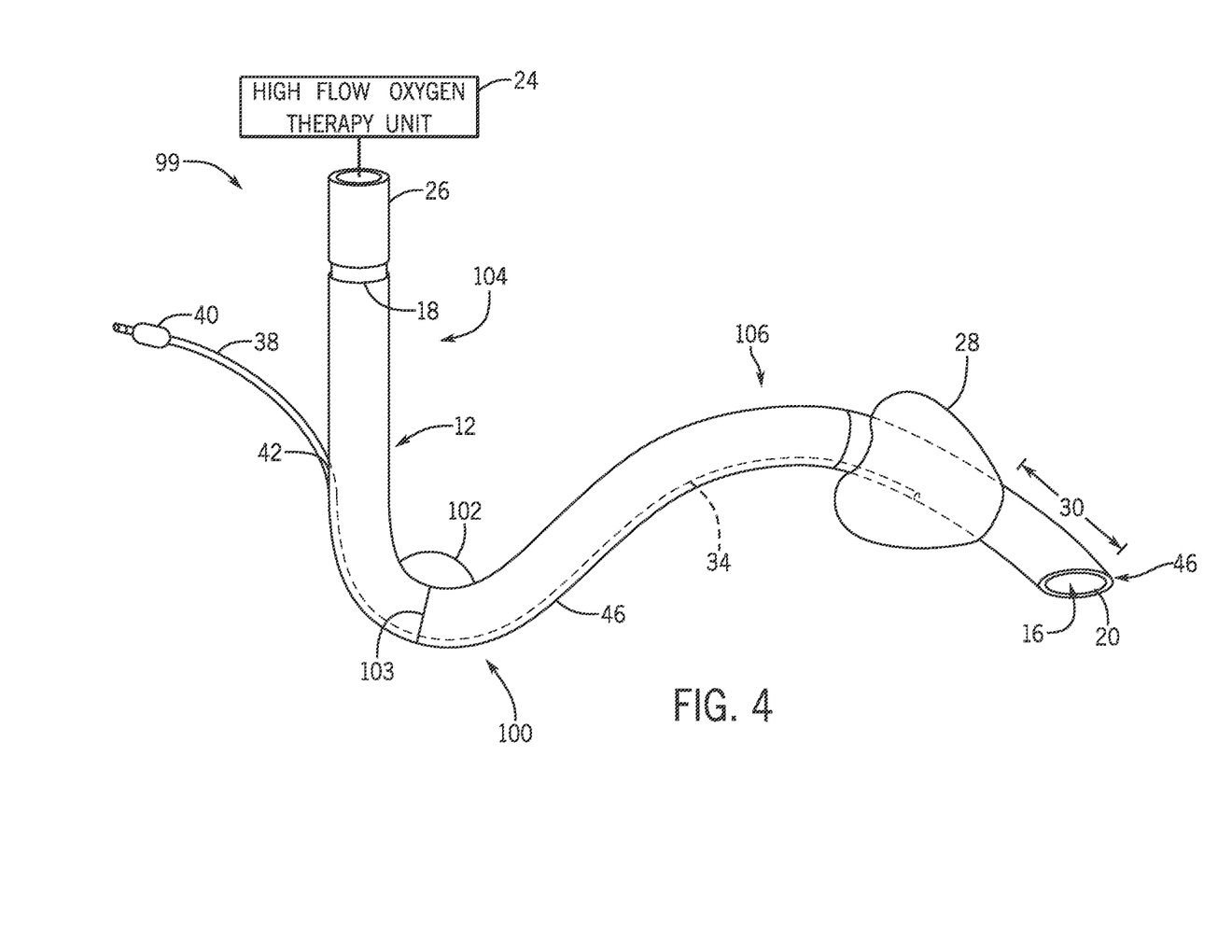
FIG. 4 is a perspective view of the cuffed nasal cannula of FIG. 1, whereby the cuffed nasal cannula is bent at an angle of approximately 90 degrees midway along its length, in accordance with an embodiment of the present disclosure

The nasal cannula 10 may have a curvature or preformed bend that facilitates positioning the nasal cannula 10 within the patient's pharynx region 68. For example, FIG. 4 illustrates an embodiment of a nasal cannula 99 having a bend or turn 100. The bend 100 may mitigate kinking and obstruction of the nasal cannula 99 and may further indicate a designated stopping point for insertion of the nasal cannula 99. Accordingly, in certain embodiments, the exterior wall 46 is provided with an indicator 103 indicating the bend point. In an embodiment, the preformed bend 100 is formed such that an interior angle 102 formed by the bend 100 is approximately equal to or less than 90 degrees. However, in other embodiments, the angle 102 may be greater than 90 degrees. By way of non-limiting example, the angle 102 may be approximately 75, 80, 85, 95, 100, 105, 110 degrees. When positioned within the patient's oral cavity, the connector 26 of the nasal cannula 99 is positioned away from the patient's nose (e.g., in a direction toward the patient's forehead). When the nasal cannula 99 is properly positioned within the patient's nasal cavity, the bend 100 is positioned against the patient's nostril. In this way, a proximal region 104 of the nasal cannula 99 positioned external to the patient may not obstruct and/or restrict access to the patient's oral cavity when in use. Distal of the bend 100, the nasal cannula 99 has an addition curved region 106 that conforms to a curvature of the patient's anatomy between the nasal cavity and the pharynx region.

Figure 5:
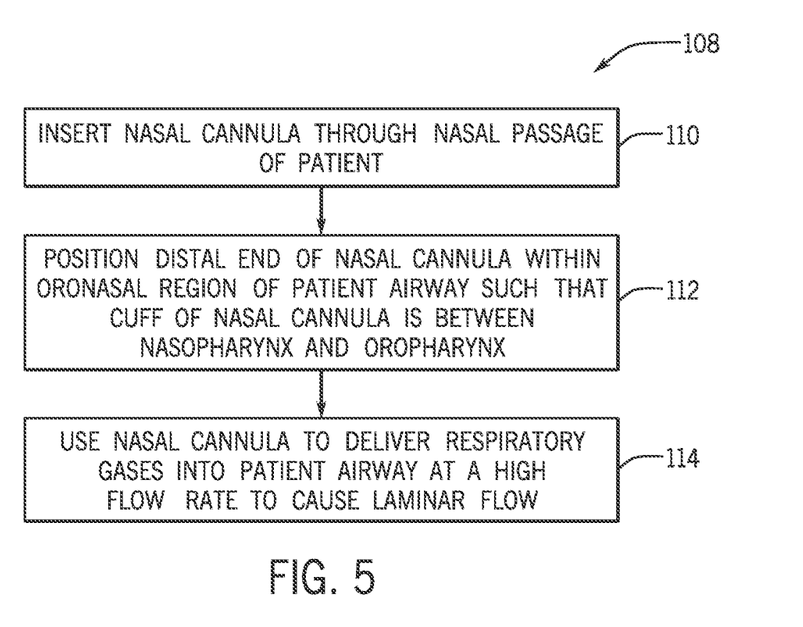
FIG. 5 is a flow diagram of a method of using the cuffed nasal cannula of FIG. 1, in accordance with an embodiment of the present disclosure.

Present embodiments also include techniques that may be used to provide ventilation or oxygen therapy, such as HFOT, using the nasal cannula 10, 99. One approach is depicted in FIG. 5, which illustrates an embodiment of a method 108 for treating a patient with HFOT using the nasal cannula disclosed herein. The method 108 includes inserting a nasal cannula (e.g., the nasal cannula 10, 99) into a patient's nose and through a nasal passage of the patient (block 110). For example, as shown in FIGS. 2 and 3, the nasal cannula 10, 99 is inserted into the nose 80 of the patient 60 and through the nasal cavity 66.

The method 108 also includes positioning a distal end of the nasal cannula within a pharynx region (e.g., the pharynx region 68) of the patient's airway such that a distal end of the nasal cannula is between the nasopharynx and the oropharynx of the patient (block 112). In embodiments of the method 108 in which the nasal cannula is cuffed, a cuff (e.g., the cuff 28) of the nasal cannula is positioned between the nasopharynx and the oropharynx of the patient. However, it should be understood that the method 108 may also be implemented with a nasal cannula as provided herein and that does not include a cuff 28. The pharynx region 68 is the region of the patient's throat that is behind the mouth and nasal cavity, and above the esophagus and larynx of the patient. The nasopharynx 70 is the area of the pharynx that includes the space between internal nares and soft palate of the patient, and the oropharynx 72 is behind the oral cavity and extends from the uvula to a level of the hyoid bone of the patient. Therefore, when present, the cuff 28 is positioned between the oropharynx 72 and the nasopharynx 70 such that, when inflated, a portion of an outer wall of the cuff 28 abuts the patient's soft palate and another portion of the outer wall of the cuff 28 abuts the patient's throat. Accordingly, the cuff 28 of the nasal cannula may be inflated to seal the passage between the nasopharynx and the oropharynx. For example, as shown in FIGS. 2 and 3, the cuff 28 of the nasal cannula 10 is inflated such that exterior wall of the cuff 28 abuts the patient's tissue along a portion of the passageway between the nasopharynx 70 and the oropharynx 72 of the patient 60. In this way, the inflated cuff 28 secures the nasal cannula 10 and seals the passageway. Moreover, the inflated cuff 28 maintains the nasal cannula 10 in position within the pharynx region 68 throughout duration of the HFOT. As discussed above, sealing the passageway between the nasopharynx 70 and the oropharynx 72 decreases a volume of the participating dead space within the patient's airway by blocking passage of air 64 within the nasal cavity 66 into the patient's trachea and vice versa. In this way, the patient 60 may not rebreathe $CO_2$-enriched gas that occupies the nasal cavity 66.

The method 108 further includes using the nasal cannula to deliver respiratory gases into the patient's airway via the nasal cannula from the distal end at a sufficiently high flow rate to cause laminar flow (block 114). For example, the nasal cannula, such as the nasal cannulas illustrated in FIGS. 1-4, may be coupled to a respiratory apparatus (e.g., a HFOT unit 24) that includes a source of pressurized oxygen and air, a humidifier, a heater, and a controller or monitor. During HFOT, a flow meter/gas blender may supply a blend of oxygen and air that make up the respiratory gases 62 to a humidifier that humidifies the respiratory gases 62. Humidifying the respiratory gases 62 prior to inhalation by the patient may mitigate drying of mucous membranes and patient discomfort. As the humidified respiratory gases 62 flow toward the patient, the heater may heat the humidified respiratory gases to physiological temperature. Accordingly, the respiratory gases 62 delivered to the patient 60 via the breathing circuit (e.g., the respiratory apparatus and the nasal cannula 10, 99) mimic the body's natural process of humidifying and heating air during normal breathing. The controller of the respiratory apparatus may monitor flow rates, oxygen levels in the respiratory gases 62, humidity, temperature, and, in certain embodiments, $CO_2$ in exhaled air, as discussed in further detail below with reference to FIG. 6. In certain embodiments, the controller may deliver the respiratory gases to the patient at a flow rate of between approximately 30 L/min and approximately 80 L/min.

For example, maintaining the incoming flow of the respiratory gases 62 more smooth and laminar may reduce the disruption of the opposite flow of the $CO_2$-rich exhaled gas 86. As a result, there may be less mixing of the outgoing $CO_2$-rich gas 86 the incoming respiratory gas 62, leading to less re-breathing of $CO_2$. In this way, the $CO_2$-rich exhaled gas 86 may be efficiently removed through the patient's oral cavity. In an embodiment, the incoming flow of the respiratory gases 62 remains in laminar flow when exiting the conduit 12 and flowing into the patient's throat (e.g., the oropharynx 72 and trachea). Unlike the irregular configuration of the nasal cavity 66, the patient's throat has a geometry similar to that of the conduit 12 and, therefore, is more structurally suited to maintain the laminar flow of the respiratory gases 62 as they continue into the lungs.

Present embodiments also include integrating HFOT with sidestream end tidal $CO_2$ ($EtCO_2$) monitoring (e.g., capnography). As discussed above, the respiratory apparatus may include a monitor used for sidestream $EtCO_2$ monitoring. Devices used in sidestream $EtCO_2$ monitoring generally use single lumen catheters that draw a sample of the patient's exhaled breath into the monitor to measure the concentration of $CO_2$ in the patient's exhaled breath. However, during HFOT, placement of the catheter near the patient's mouth or nose to capture the patient's exhaled gas may be ineffective, as the high flow rates (such as between 30 L/min and 80 L/min) of incoming gas can wash out and dilute the patient's exhalation, leading to correspondingly low levels of detected $CO_2$. Further, in contrast to respiratory therapies that provide a timed respiratory cycle with gas delivery during inhalation and not during exhalation, HFOT may be applied continuously, i.e., with a continuous flow of delivered respiratory gases. Accordingly, during HFOT, there may not be breaks in gas flowing out of the nasal cannula that correspond with patient exhalations and to which the measurement of $CO_2$ may synchronized to reduce the impact of dilution of exhaled $CO_2$ by incoming respiratory gases.

However, as provided herein, a dual lumen catheter may be used for sidestream $EtCO_2$ monitoring in conjunction with HFOT, e.g., continuous HFOT, for improved sidestream $CO_2$ monitoring. For example, a dual lumen catheter disclosed herein is configured in a manner that enables sampling of the patient's exhaled gas (e.g., the $CO_2$-rich exhaled gas 86) within the pharynx region 68 at or near the nasopharynx of the patient and while respiratory gas is simultaneously exiting the nasal cannula. That is, the dual lumen catheter collects a gas sample of the patient's exhaled gases at a location within the pharynx region 68, rather than at a location external to the patient, such as the patient's nostrils or lips. Further, the disclosed embodiments provide sidestream monitoring with an enriched gas sample collected that is not diluted by the incoming respiratory gases to provide a more accurate measurement of $EtCO_2$ in the patient's exhaled gases compared to catheters that sample the exhaled gases at a location external to the patient.

Figure 6:
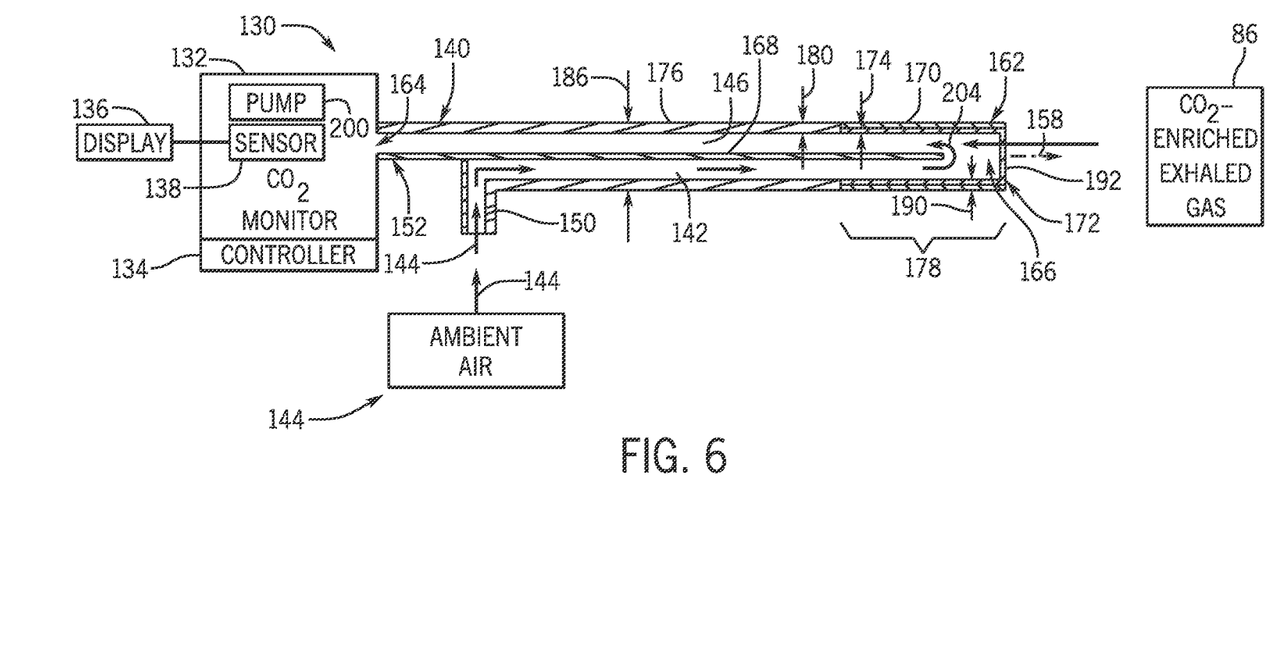
FIG. 6 is a diagram of a dual lumen catheter that is inserted into a patient and includes a carbon dioxide ($CO_2$) permeable membrane at a distal end, in accordance with an embodiment of the present disclosure

FIG. 6 illustrates a respiratory system 130 that may be used for sidestream $EtCO_2$ monitoring, including during HFOT. In the illustrated embodiment, the respiratory system 130 includes a $CO_2$ monitor 132 (e.g., a capnograph) and a cannula 140. The $CO_2$ monitor 132 operates according to instructions from a controller 134, and include various input/output features as well as a coupled or integral display 136 configured to display measured $CO_2$ levels in the exhaled breath based on output from a $CO_2$ sensor 138. The $CO_2$ sensor 138 provides a $CO_2$ measurement indicative of the $CO_2$ in the exhaled breath. The $CO_2$ measurement may be displayed on the display 136 or otherwise provided to a caregiver. The cannula 140 is a dual lumen cannula and includes a fresh gas intake lumen 142 and a $CO_2$ sampling lumen 146. The gas intake lumen 142 includes an intake port 150 that is open to ambient air 144 or any other suitable gas source that has limited $CO_2$ concentration (e.g., oxygen, respiratory gases). For example, in the illustrated embodiment, the intake port 150 is positioned slightly distal to a proximal end 152 of the cannula 140. However, in other embodiments, the intake port 150 may be at and/or form the proximal end 152 of the cannula 140. In the illustrated embodiment, the intake port 150 is illustrated as being orthogonal to a longitudinal axis 158 of the cannula 140. However, the intake port 150 may be oriented at an acute angle relative to the longitudinal axis 158. By way of non-limiting example, the intake port 150 may be oriented at 5, 10, 15, 20, 30, 45, 50, 60, 75, 80, or any other suitable acute angle relative to the longitudinal axis 158.

The sampling lumen 146 extends from the distal end 162 (e.g., a distal terminus) of the cannula 140 back to the proximal end 152 alongside at least a portion of the gas intake lumen 142. In the illustrated embodiment, a gas outlet 164 of the gas sampling lumen 146 is at and forms part of the proximal end 152 of the cannula 140. In an embodiment, the gas outlet 164 is proximal of the intake port 150. However, in certain embodiments, the gas outlet 164 of the sampling lumen 146 is distal to the intake port 150. A divider 168 (e.g., an interior wall, partition) separates and defines at least a portion of an interior wall of each of the lumens 142, 146. The lumens 142, 146 co-terminate at the distal end 162 and are in fluid communication with one another through an opening or gap 166 between the divider 168 and the distal end 162. In one embodiment, one or more through passages additionally or alternatively may be formed in the divider 168 to facilitate the flow of ambient air from the intake lumen 142 into the gas sampling lumen 146.

A $CO_2$-permeable membrane 170 is positioned at the distal end 162 of the cannula 140. The $CO_2$-permeable membrane 170 covers a distal opening 172 of the cannula 140 (e.g., an opening of each respective lumen 142, 146). The $CO_2$-permeable membrane 170 may be part of a sleeve, cap, or cover that closes the distal end 162 of the cannula 140. The sleeve may extend any suitable distance along the cannula 140 and away from the distal end 162. By way of non-limiting example, the sleeve may extend between approximately 1 cm and approximately 10 cm away from the distal end 162 and toward the proximal end 52 of the cannula 140. In certain embodiments, the sleeve may include a portion (e.g., a distal portion) that is made up of the $CO_2$-permeable membrane 170 and a portion that is another material that may readily adhere to the outer surface of the cannula 140. The $CO_2$-permeable membrane 170 may be glued, heat welded, or otherwise attached to the cannula 140. Inside the cannula, the opening 166 is maintained to permit flow of the ambient air into the gas sampling lumen 146. For example, under typical gas flow pressures, the $CO_2$-permeable membrane 170 does not block the opening 166.

The cannula 140 may include certain features that may facilitate coupling or integration of the $CO_2$-permeable membrane 170. For example, in certain embodiments, a thickness 174 of a portion of an outer wall 176 of the cannula 140 at an end portion 178 may be less than a wall thickness 180 of the outer wall 176 proximal of the end portion 178. The reduced wall thickness 174 of the outer wall 176 may facilitate placement of the $CO_2$-permeable membrane 170 in a manner in which an outer wall surface 182 of the $CO_2$-permeable membrane 170 is flush with the portion of the outer wall 176 proximal to the end portion 178. That is, the cannula 140 has a substantially constant outer dimension 186 along at least a portion of the cannula 140 that extends from the intake port 150 to the distal end 162.

In certain embodiments, the wall 176 of the cannula 140 has a substantially constant thickness 180. As such, the $CO_2$-permeable membrane 170 may extend a distance that is equal to a membrane thickness 190 away from the outer wall 176. In one embodiment, the $CO_2$-permeable membrane 170 may be part of a plug that is inserted into the distal end 162.

By way of non-limiting example, the $CO_2$-permeable membrane 170 may include materials such as polypropylene oxide (PPO), selective thin film composite membranes, or any other suitable $CO_2$-permeable membrane. In addition, the $CO_2$-permeable membrane 170 may be a blended membrane of polyurethane (PU) and polyvinyl acetate (PVAc) prepared in the presence of polyethylene oxide-polypropyleneoxide-polyethylene oxide triblock copolymer (poloxamers, Pluronic). The $CO_2$-permeable membrane 170 may be a semi-rigid membrane having a shore hardness of between approximately 70 and 90. By being semi-rigid, the $CO_2$-permeable membrane 170 may have a desirable durability for continuous use within the patient's nasal/oral cavity. In certain embodiments, the $CO_2$-permeable membrane 170 exhibits selective permeability to $CO_2$ relative to oxygen ($O_2$) and/or nitrogen ($N_2$) gases found in the delivered respiratory gases, thus acting to selectively permit $CO_2$ flow into the cannula 140 while blocking or reducing entrance of oxygen and nitrogen gases. In one embodiment, the $CO_2$-permeable membrane 170 has a selectivity of at least a factor of 5 for $CO_2$ relative to $O_2$. That is, the $CO_2$-permeable membrane 170 is at least 5 times more permeable to $CO_2$ relative to $O_2$ as measured in barrer or a permeability coefficient ratio of 5 or greater of $CO_2$ relative to $O_2$. Further, the $CO_2$-permeable membrane 170 also blocks solid or liquid secretions from entering and plugging the cannula 140.

As discussed above, the cannula 140 disclosed herein may be used in conjunction with HFOT to collect a sample of the patient's breath from within the patient (e.g., from the oral cavity, nasal cavity, pharynx region), which increases the accuracy of $EtCO_2$ measurements compared to systems that sample the patient's exhaled breath at a location external to the patient. For example, in operation, the cannula 140 is inserted into the patient (e.g., into the nasal cavity, the pharynx region, the oral cavity) to collect a sample of the $CO_2$-rich exhaled gas 86 for $EtCO_2$ monitoring. A pump 200 of the $CO_2$ monitor 132 draws the ambient air through the gas intake lumen 142, as shown by arrow 144. For example, the intake port 150 is open to ambient, when the pump 200 pulls a vacuum on the cannula 140 (e.g., at the gas outlet 164) to draw the ambient air 144 through the gas intake lumen 142. The ambient air 144 flows through the gas intake lumen 142 toward the distal end 162 of the cannula 140 and flows into the gas sampling lumen 146 through the opening 166, as shown by arrow 204. Because of the presence of the $CO_2$-permeable membrane 170 at the distal end 162 of the cannula 140, the ambient air 144 in the gas intake lumen 142 is unable to exit the cannula 140 at the distal end 162. Therefore, the ambient air 144 flows into the gas sampling lumen 146, where it mixes with the sampled $CO_2$-rich exhaled gas 86.

At the distal end 162, the ambient air mixes with $CO_2$ from the patient's exhaled breath 86. The ambient air 144 carries the $CO_2$-rich exhaled gas 86 through the gas sampling lumen 146 and toward the $CO_2$ monitor 132. The pump 200 can maintain a desired gas sampling flow rate by drawing the ambient air 144 through the gas intake lumen 142 to achieve real-time $EtCO_2$ monitoring. The gas intake lumen 142 also maintains the desired pressure within the gas sampling lumen 146 such that the gas sampling lumen 146 does not collapse when the pump 200 pulls the vacuum for sampling of the $CO_2$-rich exhaled gas 86.

The $CO_2$-permeable membrane 170 limits the fluids that enter the cannula 140 through the distal end 162. Therefore, during sampling, the $CO_2$-permeable membrane 170 allows the $CO_2$-rich exhaled gas 86 to enter into the cannula 140, while blocking passage of other fluids (e.g., patient secretions and the respiratory gases 62) into the cannula 140. As such, oral/nasal fluids and/or patient secretions may not flow into the cannula 140 and block a flow of gases 86, 144 through the cannula 140. In addition to blocking undesirable fluids and patient secretions that may occlude the lumens 142, 146, the $CO_2$-permeable membrane 170 may selectively allow passage of $CO_2$ in the $CO_2$-rich exhaled gas 86 of the patient into the sampling lumen 146 for analysis in the $CO_2$ monitor 132, and block passage of the ambient air 144 out of the cannula 140. The ambient air 144 mixes with the sampled $CO_2$-rich exhaled gas 86 in the gas sampling lumen 146 and maintains a desired flow rate through the cannula 140 for real-time $EtCO_2$ monitoring.

Moreover, the disclosed cannula 140 facilitates $EtCO_2$ monitoring during HFOT. For example, during HFOT, the high flow rate of the respiratory gases 62 may dilute the $CO_2$-rich exhaled gas 86 at the patient's lips or nostrils. Accordingly, the gas sampled for $EtCO_2$ monitoring at those locations may not be representative of the patient's exhaled breath. However, by positioning the distal end 162 of the cannula 140 within the patient (e.g., within the nasal cavity, the oral cavity, pharynx region), the cannula 140 may collect a representative sample of the patient's exhaled breath with reduced dilution from the incoming HFOT flow, thereby improving $EtCO_2$ monitoring during HFOT. In addition, the $CO_2$-permeable membrane 170 blocks secretions that may occlude the sampling lumen 146 from entering the cannula 140. Accordingly, the cannula 140 may be positioned within the patient to collect the sample of the $CO_2$-rich exhaled gas 86, rather than external to the patient. In certain embodiments, the $CO_2$ monitor 132 may apply a correction factor to the measured $EtCO_2$ measurement to correct for gas dilution that may result from the $CO_2$-permeable membrane 170.

Figure 7:
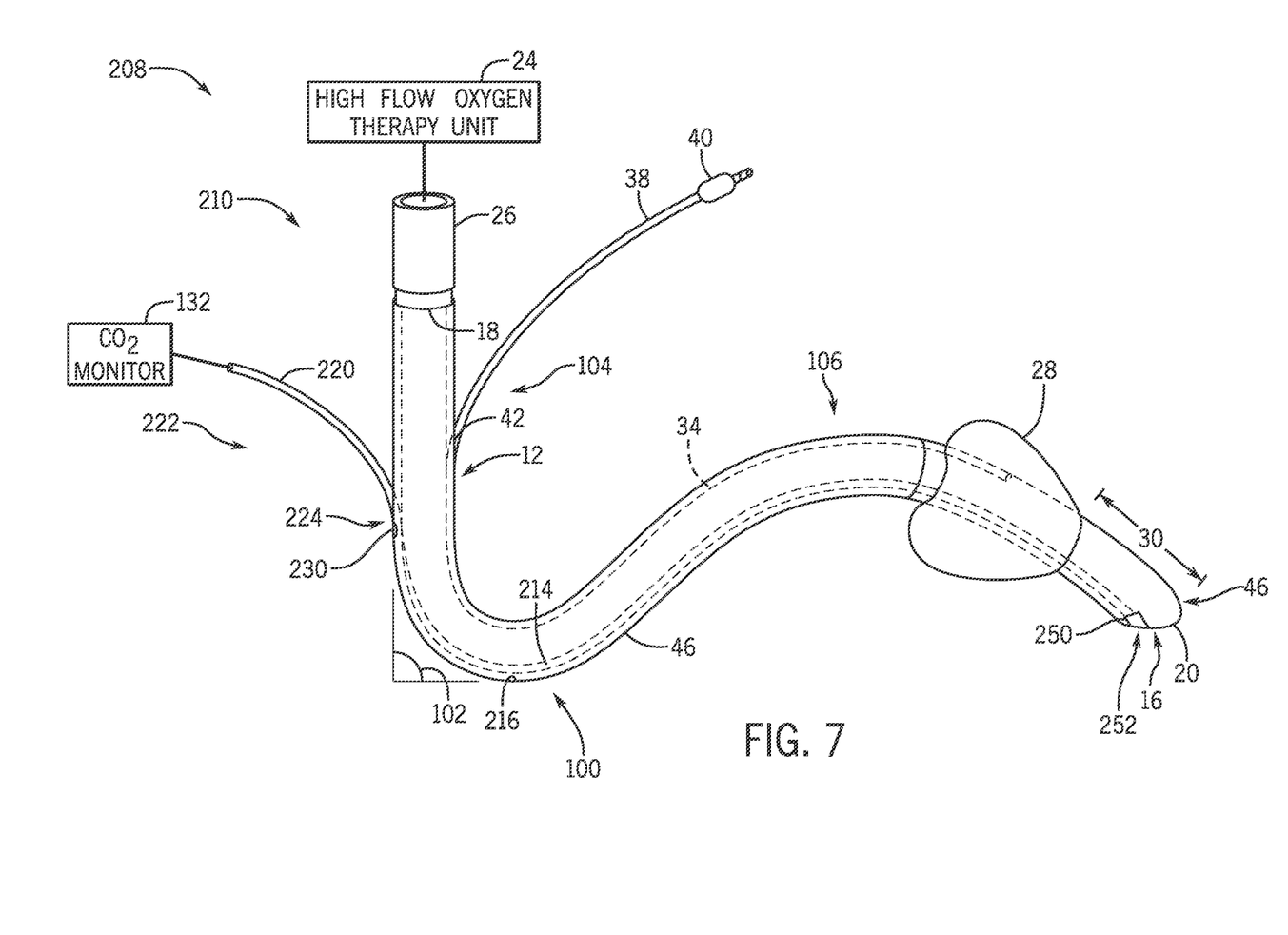
FIG. 7 is a perspective view of a cuffed nasal cannula having a gas monitoring lumen fluidly coupled to a gas intake lumen, the lumens being sealed at a distal end with a $CO_2$-permeable membrane, in accordance with an embodiment of the present disclosure.

In certain embodiments, the gas sampling lumen and the gas intake lumen of the cannula 140 may be integrated into the nasal cannula (e.g., the nasal cannula 10) of FIGS. 1-4. By integrating the breath delivery and $CO_2$ sampling lumens into a single device, $EtCO_2$ monitoring may be done without having to insert a separate cannula into the patient to sample $CO_2$. FIG. 7 illustrates a respiratory and monitoring system 208 that includes a nasal cannula 210 that may be used to deliver HFOT via the high flow oxygen therapy unit 24 of the system 208 and sample the patient's exhaled breath from within the patient. The nasal cannula 210 also includes certain features of the nasal cannula 10 discussed above with references to FIGS. 1-4. In addition, the nasal cannula 210 includes a $CO_2$ gas sampling lumen 214 and a fresh gas intake lumen 216. The lumens 214, 216 are disposed on or formed within a wall of the conduit 12 (e.g., between the outer wall 46 and an inner wall) and extend from the proximal end 18 to the distal end 20. Accordingly, a diameter of the lumens 214, 216 is less than a diameter of the central lumen 16 of the conduit 12. The gas sampling lumen 214 is fluidly coupled to a sampling line 220, which is connected (e.g., via a proximal connector) to a $CO_2$ monitor of the system 208 (e.g., the $CO_2$ monitor 132). While the $CO_2$ monitor 132 and the HFOT unit 24 are depicted as separate devices, it should be understood that the $CO_2$ monitor 132 and the HFOT unit 24 may be implemented as a single or unitary device that performs both HFOT delivery and $CO_2$ monitoring. As disclosed herein, the $CO_2$ measurement of the disclosed techniques facilitates $CO_2$ sidestream monitoring during HFOT even when incoming delivered respiratory gases are present, which might otherwise dilute or reduce $CO_2$ levels entering the sampling lumen. Because the $CO_2$-permeable membrane 250 selectively permits entry of $CO_2$ into the sampling lumen over other gases present in the airway, the sampled exhaled breath is sufficiently enriched to allow accurate monitoring by the $CO_2$ monitor 132.

Figure 8:
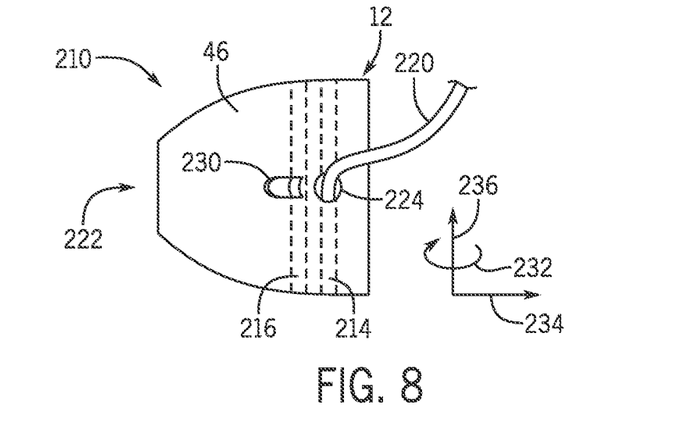
FIG. 8 is perspective view of a portion of the cuffed nasal cannula of FIG. 7 whereby the gas monitoring lumen and the gas intake lumen each have an opening on an outer wall of the cuffed nasal cannula, in accordance with an embodiment of the present disclosure.

The gas sampling lumen 214 may be formed during an extrusion process and may run along an entire length of the conduit 12. The gas sampling lumen 214 may be accessed via an opening 224 (e.g., notch) on the outer wall 46 of the conduit 12 at the point of coupling to the sampling line 220. The gas intake lumen 216 also may be accessed by an opening 230 (e.g., notch) on the outer wall 46 of the conduit 12. In one embodiment, the opening 230 is near or adjacent to the opening 224. The opening 230 enables equalization of pressure within the gas sampling lumen 214 and the sampling line 220 when a pump (e.g., the pump 200) of the $CO_2$ monitor 132 pulls a vacuum to collect a sample of the patient's exhaled breath during $CO_2$ monitoring. The openings 224, 230 are located at a proximal portion 222 of the cannula 210 that is external to the patient when the nasal cannula 210 is positioned within the patient's airway. FIG. 8 illustrates a section of the proximal portion 222 of the nasal cannula 210 having the openings 224, 230 of the lumens 214, 216, respectively, on the outer wall 46 of the conduit 12. While in the illustrated embodiment, the openings 224, 230 are spaced apart and aligned along a circumferential direction 232, in other embodiments, the openings 224, 230 may not be aligned. For example, the opening 224 may be radially 234 and longitudinally 236 spaced apart from the opening 230 such that the opening 224 is offset from and above or below the opening 230.

Figure 9:
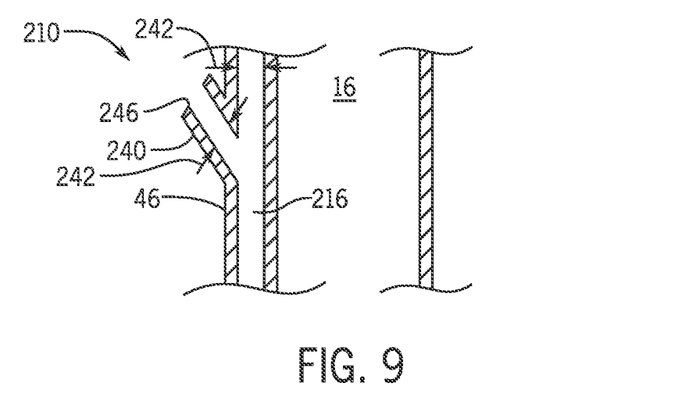
FIG. 9 is a cross-sectional view of a portion of the cuffed nasal cannula of FIG. 7, whereby the gas intake lumen includes a port extending from an outer wall of the cuffed nasal cannula, in accordance with an embodiment of the present disclosure.

The openings 224, 230 may be any suitable shape and size that enable coupling between the sampling line 220 and the gas sampling lumen 214, and fluid communication between ambient and the gas intake lumen 216, respectively. In one embodiment, the opening 230 may include a port 240 molded onto the outer wall 46 of the conduit 12, as shown in FIG. 9. The port 240 may enable a constant diameter 242 along a length of the gas intake lumen 216 from an opening 246 to a distal end of the gas intake lumen 216. In one embodiment, the opening 246 may include a mesh to block debris or other particulates from flowing into the gas intake lumen 216 during $CO_2$ monitoring.

Returning to FIG. 7, the nasal cannula 210 also includes a $CO_2$-permeable membrane 250 disposed at a distal terminus 252 of each respective lumen 214, 216. Similarly to the $CO_2$-permeable membrane 170, the $CO_2$-permeable membrane 250 blocks or selectively reduces passage of non-$CO_2$ gases (e.g., the respiratory gases 62 and ambient air 144) into and out of the lumens 214, 216, and selectively allows passage of $CO_2$ gas (e.g., the $CO_2$-rich exhaled gas 86) from the patient's airway into the lumen 214.

Figure 10:
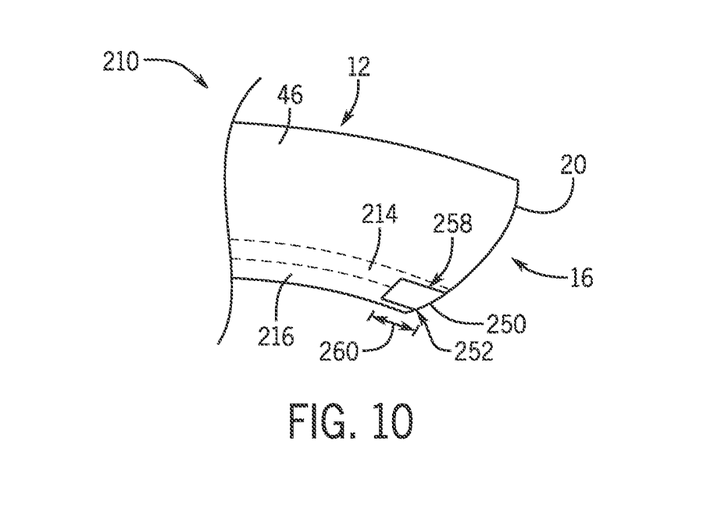
FIG. 10 is a perspective view of a distal portion of the cuffed nasal cannula of FIG. 7, whereby the $CO_2$-permeable membrane is positioned on a portion of a distal end of the cuffed nasal cannula, in accordance with an embodiment of the present disclosure.

FIG. 10 illustrates a portion of the nasal cannula 210 having the $CO_2$-permeable membrane 250 at the distal end 20 of the conduit 12. In the illustrated embodiment, the outer wall 46 may have a notch 258 along a portion of the outer wall 46 such that at least a portion of both lumens 214, 216 are removed (e.g., are not covered by the outer wall 46 of the conduit 12). The notch 258 may extend a distance 260 away from the distal end 20 (e.g., at the location of the distal terminus 252 of the lumens 214, 216) toward the proximal end 18 of the conduit 12. The notch 258 enables fluid communication between the lumens 214, 216. The $CO_2$-permeable membrane 250 seals the notch 258 to selectively block passage of patient secretions and/or reduce the passage of certain respiratory gases 62 administered to the patient (e.g., during HFOT). The $CO_2$-permeable membrane 250 may be coupled to the nasal cannula 210 via any suitable technique. By way of non-limiting example, the $CO_2$-permeable membrane 250 may be attached to the nasal cannula 210 via heat bonding, solvent bonding, or gluing. It should be understood that other configurations are contemplated. While the depicted embodiments shows an arrangement in which the $CO_2$-permeable membrane 250 is positioned at the distal terminus 252, the lumens 214, 216 may additionally or alternatively be notched or opened at other positions on the wall 46 of the cannula 210 between the distal cuff shoulder and the distal end 20 to fluidically couple the lumens 214, 216, and such notches or openings may be covered by the $CO_2$-permeable membrane 250.

By integrating the lumens 214, 216 and the $CO_2$-permeable membrane 250 into the nasal cannula 210, the patient may receive respiratory gases (e.g., the respiratory gases 62) and the patient's exhaled breath may be monitored for $CO_2$ levels using a single device (e.g., the nasal cannula 210). For example, during HFOT, the nasal cannula 210 may be positioned within the patient's pharynx region (e.g., the pharynx region 68) and respiratory gases (e.g., the respiratory gases 62) may be administered to the patient through the conduit 12 via a laminar flow, according to the acts of the method 108 of FIG. 5. When $CO_2$ monitoring is desired, a pump (e.g., the pump 200) of the $CO_2$ monitor (e.g., the $CO_2$ monitor 132) samples the patient's $CO_2$-rich exhaled gas (e.g., the $CO_2$-rich exhaled gas 86) by pulling a vacuum on the sampling line 220 and gas sampling lumen 214. Consequently, ambient air (e.g., the ambient air 144) is drawn into the gas intake lumen 216 via the opening 230, 246.

As discussed above, the $CO_2$-permeable membrane 250 selectively permits passage of $CO_2$ with greater permeability relative to the respiratory gases (oxygen, nitrogen gases in ambient air) of HFOT into the gas sampling lumen 214 and allows passage of the $CO_2$ in the patient's exhaled breath (e.g., the $CO_2$-rich exhaled gas 86) to a $CO_2$ monitor. In addition, the $CO_2$-permeable membrane 250 maintains the integrity of the sealed airway by blocking or significantly reducing oxygen and nitrogen gas exfiltration from the intake lumen 216 into the closed airway space. It should be understood that, while ambient air includes $CO_2$ at relatively low levels that may mix with the sampled $CO_2$ into the gas sampling lumen 214, these low levels may be accounted for via calibration of the $CO_2$ sensor 138 to ambient $CO_2$. The ambient air flows from the gas intake lumen 216 into the gas sampling lumen 214 and mixes with the $CO_2$ gas sampled from within the patient. The ambient air carries the $CO_2$ gas sampled from the patient to the $CO_2$ monitor at a desired flow rate for real-time $CO_2$ monitoring.

Technical effects of the invention include the use of a nasal cannula having a length that positions a distal terminus of the nasal cannula within a pharynx region of the patient (e.g., between the nasopharynx and the oropharynx). By positioning the distal terminus of the nasal cannula within the pharynx region, a flow of respiratory gases exiting the nasal cannula during high flow oxygen therapy (HFOT) may be laminar rather than turbulent. The laminar flow of the respiratory gases improves $CO_2$ washout at mitigates rebreathing of $CO_2$ monitoring enriched gases while also maintaining the desired lung pressure to allow for efficient transfer of respiratory gases into the patient's bloodstream. In addition, the nasal cannula disclosed herein includes an inflatable cuff that may be used to seal the passage between the nasopharynx and the oropharynx, thereby decreasing the dead space in the nasal cavity of the patient and rebreathing of the $CO_2$-enriched gases within the dead space while also maintaining an open (i.e., unsealed) oral passage to permit exhalation of $CO_2$-enriched gases through the oral passage. Certain embodiments also include placing a $CO_2$-permeable membrane at the distal terminus of the nasal cannula, or an oropharynx cannula to facilitate and improve sidestream $CO_2$ monitoring during HFOT.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, it should be understood that certain elements of the disclosed embodiments may be combined or exchanged with one another.

What is claimed is:

1. A method of high flow oxygen therapy (HFOT) and carbon dioxide ($CO_2$) monitoring comprising:
   delivering high flow oxygen therapy (HFOT) via a central lumen of a nasal cannula, the nasal cannula comprising a proximal end, a distal end positioned within a pharynx region of a patient's airway, and the central lumen, and further comprising an inflatable cuff coupled to an exterior wall of the nasal cannula to anchor the distal end within the pharynx region and a sampling lumen formed within a wall of the nasal cannula, the sampling lumen terminating in a carbon dioxide ($CO_2$) permeable membrane positioned at or near the distal end of the nasal cannula, and wherein the $CO_2$-permeable membrane is selectively permeable to $CO_2$ relative to oxygen, wherein the nasal cannula further comprises a second lumen fluidically coupled to the sampling lumen and configured to receive ambient air via an opening wherein the second lumen extends from an opening on the exterior wall of the conduit and co-terminates with the sampling lumen such that a distal terminus of the second lumen is covered by the $CO_2$-permeable membrane;

receiving sampled exhaled breath of the patient via the sampling lumen at a $CO_2$ monitor, wherein the sampling lumen is configured to sample the exhaled breath at the pharynx region through the $CO_2$-permeable membrane and direct the sampled exhaled breath to a $CO_2$ monitor fluidly coupled to the sampling lumen; and determining a level of $CO_2$ in the exhaled breath using the $CO_2$ monitor.

2. The method of claim 1, wherein delivering HFOT comprises delivering respiratory gas having a flow rate between approximately 30 liters/minute (L/min) and approximately 80 L/min through the central lumen.

3. The method of claim 1, wherein delivering HFOT comprises delivering respiratory gas having a flow rate between approximately 30 liters/minute (L/min) and approximately 60 L/min through the central lumen.

4. The method of claim 1, wherein delivering HFOT comprises delivering respiratory gas out of the distal end of the nasal cannula such that the delivered respiratory gas exits the distal end within the pharynx region with laminar flow.

5. The method of claim 1, wherein the $CO_2$-permeable membrane is selectively more permeable to carbon dioxide than oxygen by a factor of at least 5.

6. The method of claim 1, wherein determining a level of $CO_2$ in the exhaled breath using the $CO_2$ monitor comprises calibrating a sensor of the $CO_2$ monitor to a level of ambient $CO_2$ present in the sampling lumen.

7. The method of claim 1, wherein delivering HFOT occurs while receiving sampled exhaled breath.

8. The method of claim 1, wherein a distal-most edge of the inflatable cuff is positioned between approximately 1 cm and approximately 4 cm away from the distal end of the nasal cannula.

9. A nasal cannula for high flow oxygen therapy (HFOT), comprising:
a conduit comprising a proximal end and a distal end, wherein a length of the conduit extending between the proximal end and the distal end is between approximately 6.5 centimeters (cm) and approximately 23 cm;
an inflatable cuff coupled to an exterior wall of the conduit and positioned at or near the distal end;
a sampling lumen disposed within a wall of the conduit and configured to be coupled to a carbon dioxide ($CO_2$) monitor;
a $CO_2$-permeable membrane disposed at the distal end of the conduit and covering a distal terminus of the sampling lumen; and a second lumen disposed within the wall of the conduit and configured to direct a flow of ambient air to the sampling lumen, wherein the second lumen extends from an opening on the exterior wall of the conduit and co-terminates with the sampling lumen such that a distal terminus of the second lumen is covered by the $CO_2$-permeable membrane, and wherein the second lumen is fluidly coupled to the sampling lumen.

10. The nasal cannula of claim 9, comprising a connector disposed at the proximal end of the conduit, wherein the connector is configured to couple the sampling lumen to the $CO_2$ monitor.

11. The nasal cannula of claim 9, wherein a distal-most edge of the inflatable cuff is positioned between approximately 1 cm and approximately 4 centimeters away from the distal end of the conduit when the inflatable cuff is not inflated.

12. The nasal cannula of claim 9, wherein the inflatable cuff is asymmetric about a lumen of the conduit such that the inflatable cuff has a larger volume portion adjacent an interior curve of the conduit.

13. The nasal cannula of claim 12, wherein the $CO_2$-permeable membrane is selectively more permeable to carbon dioxide relative to oxygen by a factor of at least 5.

14. The nasal cannula of claim 9, wherein second lumen is separated from the sampling lumen by an internal divider along at least a portion of its length, and wherein the ambient air enters the sampling lumen from the second lumen via a notch or opening in the internal divider or a gap between a divider terminus and the $CO_2$-permeable membrane.

15. A high flow oxygen therapy (HFOT) system comprising:
a gas source providing a source of oxygen for delivery to a patient in high flow oxygen therapy (HFOT); and
a conduit coupled to the gas source and comprising:
a first lumen extending between a proximal end and a distal end of the conduit, wherein the first lumen is configured to sample a patient's breath during exhalation;
a carbon dioxide ($CO_2$)-permeable membrane disposed on the distal end of the conduit, wherein the $CO_2$-permeable membrane is configured to selectively allow passage of $CO_2$ gas from the patient's airway into the conduit during exhalation, wherein the $CO_2$-permeable membrane is selectively permeable to $CO_2$ relative to oxygen; and
a second lumen fluidly coupled to the first lumen, wherein a distal terminus of the second lumen is covered by the $CO_2$-permeable membrane, and wherein the second lumen is configured to receive ambient air.

16. The HFOT system of claim 15, wherein the second lumen extends from the distal end and comprises an opening distal to the proximal end of the conduit, wherein the opening is configured to receive and direct the ambient air to the second lumen.

17. The HFOT system of claim 15, wherein the conduit comprises a connector configured to couple the first lumen to a capnograph, the capnograph configured to measure end tidal $CO_2$ ($EtCO_2$) in the patient's breath via detection of $CO_2$ in the first lumen.

18. The HFOT system of claim 15, wherein the conduit comprises a third lumen extending to the distal end of the conduit along at least a portion of the conduit and configured to deliver respiratory gases into the patient's airway, wherein a diameter of the third lumen is greater than a diameter of the first and second lumens.

19. The HFOT system of claim 15, further comprising a capnograph comprising a $CO_2$ sensor configured to detect the $CO_2$ in the patient's breath.

* * * * *